United States Patent [19]

Oe

[11] Patent Number: 5,065,435
[45] Date of Patent: Nov. 12, 1991

[54] METHOD AND APPARATUS FOR ANALYZING VENTRICULAR FUNCTION

[75] Inventor: Mitsuo Oe, Ootawara, Japan

[73] Assignee: Kabushiki Kaisha Toshiba, Kawasaki, Japan

[21] Appl. No.: 435,741

[22] Filed: Nov. 14, 1989

[30] Foreign Application Priority Data

Nov. 16, 1988 [JP] Japan .................................. 63-289255

[51] Int. Cl.$^5$ .............................................. G06K 9/00
[52] U.S. Cl. ......................................... 382/6; 282/22; 364/413.13
[58] Field of Search ...................... 382/6, 8, 54, 22, 23; 364/413.13, 413.14, 413.15, 413.22

[56] References Cited

U.S. PATENT DOCUMENTS

| | | | |
|---|---|---|---|
| 3,869,602 | 3/1975 | Sezaki et al. | 382/6 |
| 4,333,145 | 6/1982 | Heuscher et al. | 382/6 |
| 4,843,630 | 6/1989 | Catros et al. | 382/6 |

OTHER PUBLICATIONS

Sheehan et al., "Diagnostic Methods—Ventricular Performance" 74 Circulation No. 2, 293-305, (Aug. 1986).
Sigel et al., "Interobserver and Intermethod Variation in Evaluation of Regional Wall Motion of the Left Ventricle", 6 Cardiovasc Intervent Radiol., 14-19, (1983).

*Primary Examiner*—Michael Razavi
*Attorney, Agent, or Firm*—Finnegan, Henderson, Farabow, Garrett, and Dunner

[57] ABSTRACT

A method for analyzing ventricular function comprises the steps for generating ED contour image data representing the contour of the heart in an end diastole (ED) phase and an ES contour image data representing the contour of the heart in an end systole (ES) phase, generating a graph of an average cardiac function of the normal heart, and generating a standard heart ES contour (or ED contour) image from the ED contour image or the S contour image of the subject heart, to be examined, by the graph of average cardiac function of the normal heart. The ED contour image data or ES contour image data of the heart of a subject to be examined is superimposed on the standard heart ES contour or the ED contour image data, to analyze the ventricular function of the subject from a state of superimposition between the contour image data of the subject's heart and the standard heart contour image data.

16 Claims, 4 Drawing Sheets

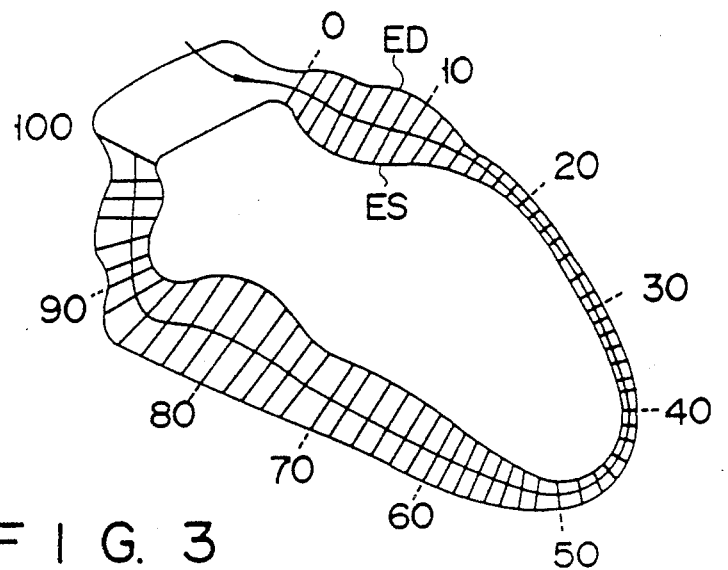
F I G. 3
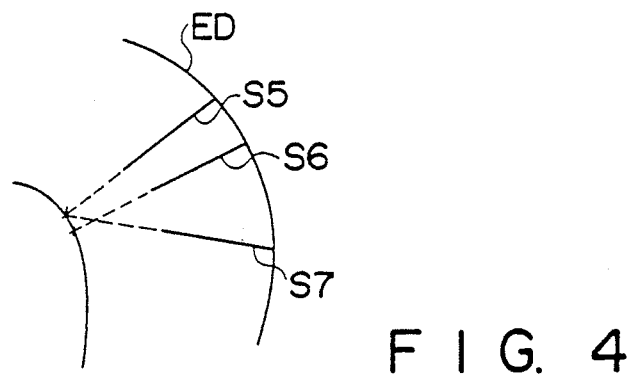
F I G. 4
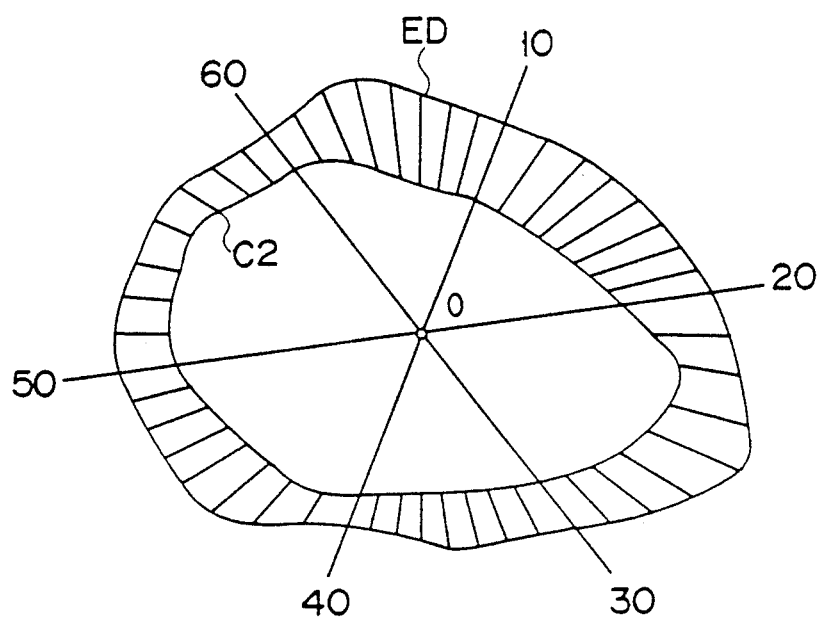
F I G. 5

METHOD AND APPARATUS FOR ANALYZING VENTRICULAR FUNCTION

BACKGROUND OF THE INVENTION

The present invention relates to a method and apparatus for analyzing a regional ventricular function of a subject heart using a center line method.

2. Description of the Related Art

A proposal has been made for analyzing regional ventricular function and diagnosing the cardiac function of a subject. In particular, the center line method has generally been employed in view of its favorable clinical results. This technique is disclosed in "Diagnostic Methods-Ventricular Performance, Sheehan et al. Circulation Vol. 74, No. 2 Aug. 1986". According to this method, the heart is continuously imaged through, for example, an X-ray DF (digital fluorography) apparatus for angiography to obtain a contour image of the heart in an end diastole (ED) phase, that is an ED contour image, and a contour image of the heart in an end systole (ES) phase, that is the ES contour image. The ED and ES contour images are superimposed in a manner to align with their lines connecting the midpoint of the aortic valve to the apex. A line passing between the contour images, i.e. center line is drawn. A plurality of lines which are orthogonal to the center line are drawn at an equal interval along the center line from the ED contour image to the ES contour image. These lines are called "contraction chords" representing the extent to which the heart contracts. The length of the chords are measured to find a corresponding rate of contraction. A graph is prepared with the rate of contraction as ordinate and the number of chords along the center line as abscissa. The cardiac function graph is compared with the normal cardiac function graph to diagnose the ventricular function.

According to the aforementioned method, a cardiac function graph is prepared from the patient's cardiac contour image and the patient's cardiac function graph is compared with the normal cardiac function graph to evaluate whether or not the cardiac function of the patient falls within the standard deviation. However, it is not possible to diagnose any abnormal region in the patient's heart unless such an evaluation is initially made. That is, diagnosis cannot be made directly from the patient's cardiac contour image, failing to diagnose prompt cardiac function.

SUMMARY OF THE INVENTION

The present invention is to provide a method and apparatus for analyzing regional ventricular function directly from a cardiac contour image.

In one aspect of the present invention there is provided a method for analyzing ventricular function, comprising the steps of forming an ED contour image representing a contour of the subject heart in an end diastole (DE) phase and an ES contour image in an end systole (ES) phase; forming a cardiac motion contour image, using the ED contour image and the ES contour image; generating a graph of an average cardiac function of the normal heart; generating a standard cardiac motion contour image obtained by the the graph of average cardiac function of the normal heart with the ED contour image or the ES contour image being set as a base; and superimposing the cardiac motion contour image on the standard cardiac motion contour image to analyze the ventricular function from the superimposed state of the cardiac motion contour image of the subject heart and the standard cardiac motion contour image.

In another aspect of the present invention, there is provided an apparatus for analyzing ventricular function, comprising means for forming an ED contour image representing a contour of the subject heart in an end diastole (DE) phase and an ES contour image in an end systole (ES) phase. Means for forming a cardiac motion contour image, using the ED contour image and the ES contour image means to generate a graph of an average cardiac function of the normal heart; means for generating a standard cardiac motion contour image obtained by the graph of average cardiac function of the normal heart with the ED contour image or the ES contour image being set as a base; means for superimposing the cardiac motion contour image on the standard cardiac motion contour image; and means for analyzing the ventricular function from the superimposed state of the cardiac motion contour image of the subject heart and the standard cardiac motion contour image.

BRIEF DESCRIPTION OF THE DRAWINGS

FIGS. 2 and 3 are views for explaining a method for determining a standard deviation contour;

FIG. 4 is a view explaining the processing of charades when they cross each other;

FIG. 5 is a view explaining a method of the present invention;

DETAILED DESCRIPTION OF THE PREFERRED EMBODIMENTS

Figure 1:
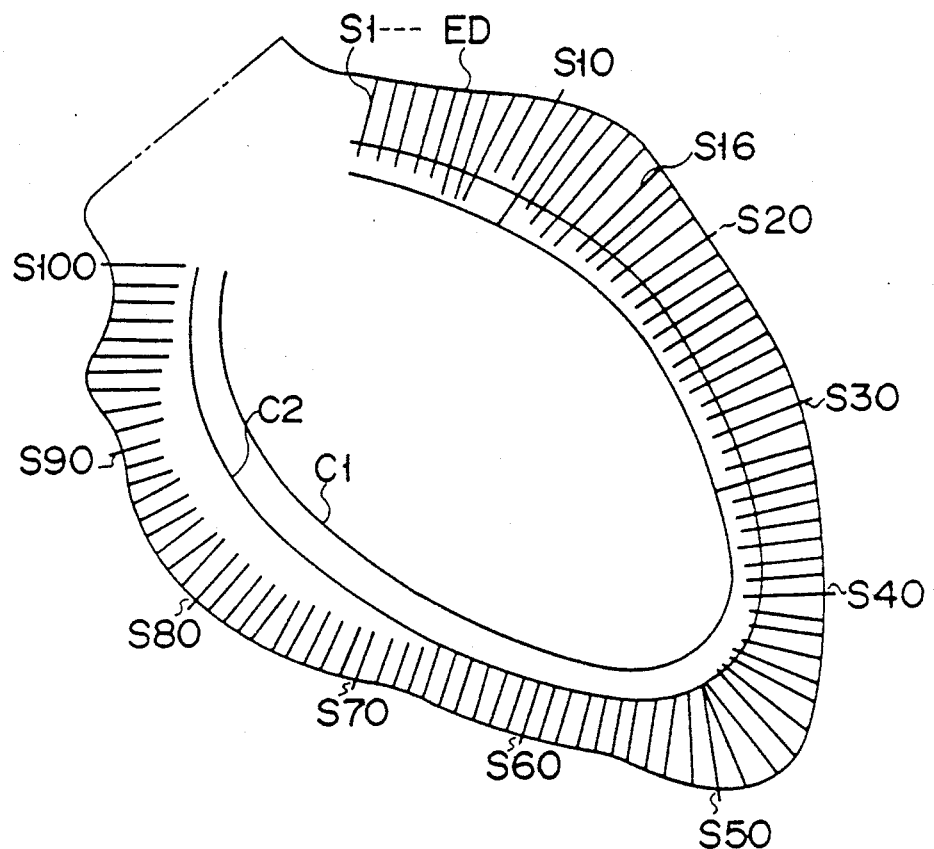
FIG. 1 is a view for explaining a ventricular function analytic method according to one embodiment of the present invention.

FIG. 1 is a view showing the heart of a patient whose cardiac motion contour image is superimposed on a standard cardiac contour image. The patient's cardiac motion contour image is obtained by preparing a cardiac contour image (DE contrast image) of an end diastole (ED) phase and cardiac contour image (ES contract image) of an end systole phase from the heart's fluorographic image obtained by, for example, circulator X-ray DF apparatus and superimposing the ED and ES contour images one over the other.

In FIG. 1, Cl and C2 represent the upper and lower limit levels, respectively, of a standard deviation of the contraction motion of the normal heart from the average level. The contour of the standard upper and lower limit levels of the aforementioned deviation are initially found in the following way.

Figure 2:
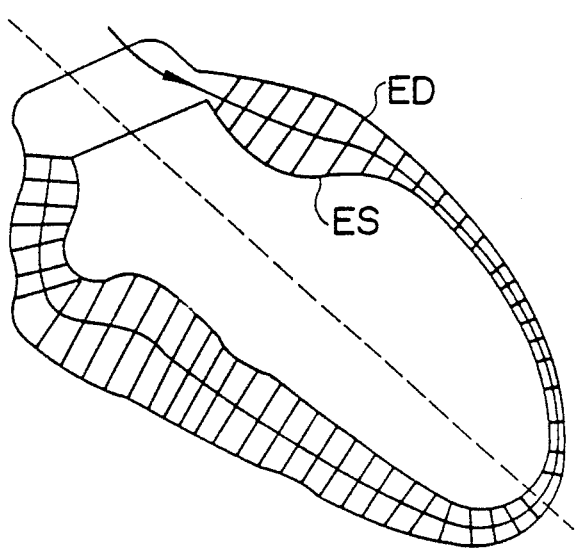

First, the fluorographic images of the heart are continuously imaged by the DF apparatus, etc. and the ED and ES contour images are prepared, as graphic data, based on the fluorographic images. The ED and ES contour imaged are moved rotationally and in parallel way with their major axes of the two contours aligned with each other in a superimposed fashion to prepare a cardiac motion contour image as shown in FIG. 2. In this motion contour image, the border of the ED contour image is divided, for example, into 100 equal parts except for the aortic valve. 100 straight lines are drawn from the 100 equal points on the ED contour image to the ES contour image in a manner perpendicular to the ED contour image. A midpoint is determined relative to the straight image. and a center line is drawn between the ED and ES contour images with the midpoints connected to each other.

As shown in FIG. 3, the 100 straight lines which are crossed at right angles to the center line are drawn along the center line from the ED contour line to the ES contour line at an equal interval, and contraction chords are formed on the standard cardiac motion contrast image. The contraction chords are seguentially numbered with numbers 1 to 100 in a clockwise direction as shown in FIG. 3, noting that the numbers are given in increments of 10.

Figure 7:
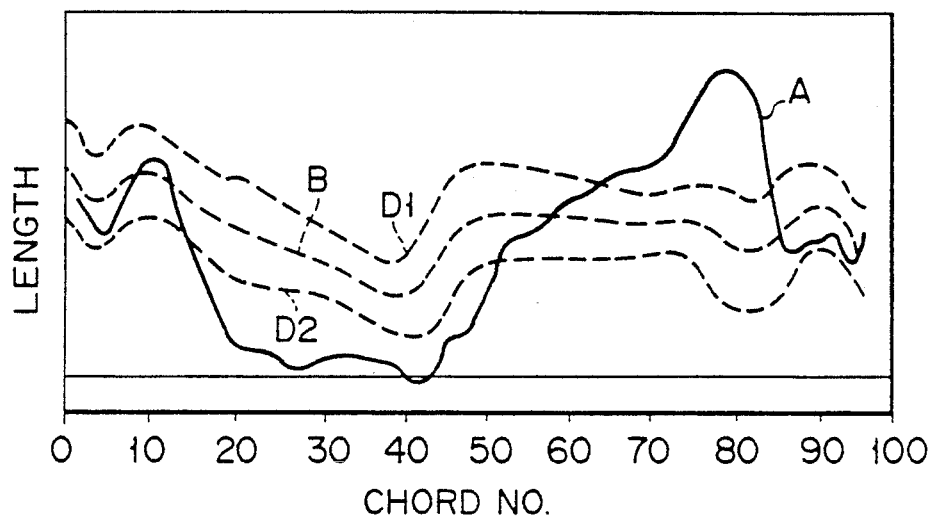
FIG. 7 is a cardiac function graph.

The length of the chords is normalized with the length of the circumference of the ED contour to represent a cardiac function graph as shown in FIG. 7 as A, where the abscissa represents the chord numbers 0 to 100 and the ordinate represents the length of the normalized chords.

A graph representing an average valve B of the normally contacted heart and upper and lower limit valves D1 and D2 are superimposed on the graph as set forth above.

Figure 8:
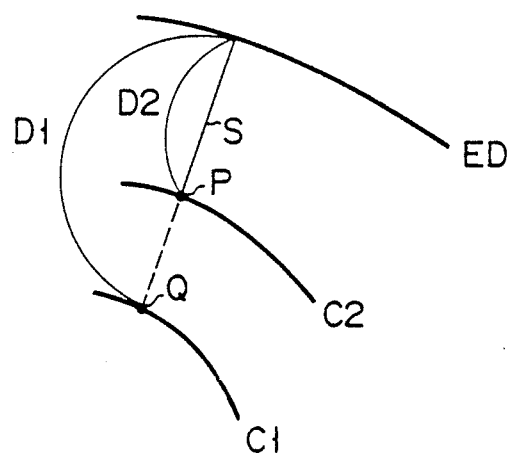
FIG. 8 is a view explaining a method of the present invention for forming Contours Cl and C2 of a normal range.

By the graph of the upper and lower limit valves D1 and D2, the contours C1 and C2 of the normal range are prepared with a method according to FIG. 8. That is, a point Q on the length of the contour D1 and point P on the length of the contour D2 are plotted on the line of the chords S in an interval direction from the ED contour. The points are calculated on all of the chords and the points on the chords are connected together to prepared the contours C1 and C2.

The contours C1 and C2 represent a normal contraction range when the ED contour is used as the reference. The lengths of these chords are normalized with the length of a circumference of the ED contour and represented as such on the cardiac function graph shown in FIG. 7 as A. The average valve B of the normal contracting heart and upper and lower limit valves D1 and D2 of the standard deviation are superimposed on the graph to allow a comparison to be made with the normal valve.

The cardiac contour image having a range of standard deviation (Cl, C2) from the average of the motions of the normal heart is superimposed over the cardiac contour image of the patient including a plurality of chords 1, ....S100. It is determined whether or not the chords S1 ...S100, fall within a range of standard deviation (Cl, C2). It is thus possible to determine any abnormal spot or region of the heart. Since, as shown in FIG. 1, the chords S1 to S10 reach the standard contour C2, it will be seen at first glance that the heart region corresponding to the chords S2 to S10 is in a normal state. It will be seen, on the other hand, that the heart region corresponding to the chords S70 to S100 is abnormal. a state where the heart's motion is small. Since the heart state can be diagnosed upon the observation of both the patient's cardiac contour image and the standard deviation contour image, the dooctor's burden can be alleviated when diagnosing of the heart for abnormality.

Upon a simple extension of the chords from the ED contour toward the standard deviation contour (Cl, C2), the chord S7 intersects with the adjacent chord S6, as shown in FIG. 4, in which case the chord 7 is not used.

The way of analyzing the ventricular function according to the other embodiment of the present invention will be explained below with reference to FIG. 5.

In this case, the gravity center 0 of the ED contour image is determined and 60 chords, for example, are drawn toward the gravity center 0. The condition of the patient's heart can be diagnosed, at first sight, according to whether or not the chords fall within the range of standard deviation contour (Cl, C2).

Figure 6:
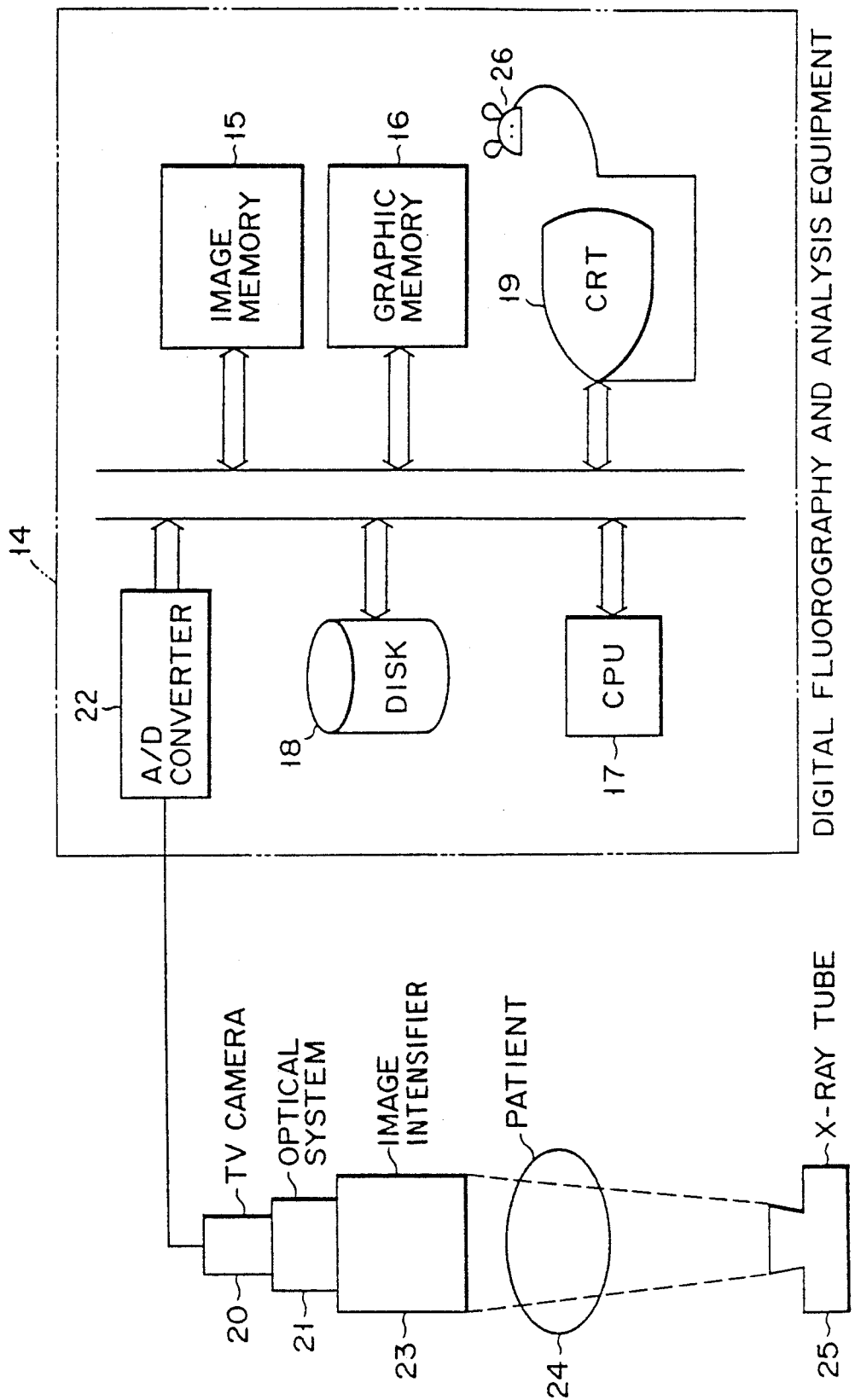
FIG. 6 is a diagrammatic view showing a ventricular function analytic apparatus which is used for carrying out the methods of FIGS. 1 and 5.

An apparatus for carrying out the aforementioned ventricular function analytic method will be explained below with reference to FIG. 6.

An X-ray which is generated from an X-ray tube 25 is input via a patient 24 to an image intensifier 23 where the X-ray is converted to an optical image. The image is supplied via an optical system 21 to a TV camera 20 where it is converted to a video signal. The video signal is converted to a digital image by an A/D converter 22 into a digital fluorography analysis equipment 14 and stored in an image memory 15. The image memory 15 stores the image data which is sequentially sent from to A/D converter 22. A graphic memory 16 is connected to a corresponding data bus to store contour image data corresponding to the cardiac image prepared by the image data stored in the image memory 15. That is, the ED and ES contour images are stored in the graphic memory 16. The contour images are prepared by reading data corresponding to the contour of the heart from the image memory 15 under the address control of CPU 17 and storing it in a corresponding address of the graphic memory 16.

A disk memory 18 stores the standard deviation data Cl, C2, such as the length data of the chords. The standard deviation contour data C1, C2 are read out from the disk memory 18 by the address designation made by CPU 17 and prepared by the aforementioned method. CRT 19 receives both the ED contour data, to be examined, stored in the graphic memory 16 and standard deviation contour data and synthesizes the subject ED contour image and standard deviation data for display.

The image data is sent via the corresponding data bus to the image memory 15 where it is stored. The image data in the image memory 15 contains a plurality of cardiac fluoroscopic images including the ED image and ES image, and only the ED and ES images are extracted from the fluoroscopic image. That is, only the data corresponding to the contours of the ED and ES images is read out from the image memory 15 and sent to the graphic memory 16 for storage. At this time, the address designation is performed by CPU 17.

The contour image data in the graphic memory 16 is read onto CRT 19 where the ED and ES contour images are displayed. At this time, the ES contour is represented by the forward ends of many chords extending inside from the ED contour as shown in FIG. 1. The standard deviation contours C1 and C2 are prepared and. after being superimposed, stored in CRT 19. By so doing the standard deviation contour images Cl and C2 are displayed such that they are superimposed over the ED contour image and chords as shown in FIG. 1. The abnormal region of the heart can be diagnosed at first glance on CRT 19 according to whether or not, in a superimposed image between the subject heart's contour image and standard deviation contour image, the chords fall within a range of standard deviation contour images Cl, C2. A mouse 26 provides means for inputting any necessary data into CRT When the standard deviation contour images C1, C2, are to be displayed on CRT 19 in a manner to be superimposed on the subject heart's ED contour image, the chord data which are sequentially read out from the disk memory 18 are output in a manner to correspond to those addresses of divided equal points on the ED contour image read out of the graphic memory 16, and a line connected to the forward ends of contour lines drawn inside from the ED contour is displayed as a standard deviation contour image on CRT 19.

In FIG. 5, the gravity center of the heart is determined and chords are drawn toward the gravity center of the heart. However, the chords may be drawn toward any arbitrary point on the heart. Further, the chords may be drawn in one given direction or may be drawn from the ES contour, not the ED contour line.

For the display of the contour image, the ED contour image and standard deviation contour image may be displayed on a color CRT in different color or may be displayed on the CRT with the ED contour image as solid lines and the standard deviation contour image as dotted lines.

What is claimed is:

1. A method for analyzing a ventricular function of a subject heart, comprising the steps of:
   forming an ED contour image representing a contour image of the subject heart in an end diastole (DE) phase and forming and ES contour image representing a contour image of the subject heart in an end systole (ES) phase;
   forming a cardiac motion contour image, using the ED contour image and the ES contour image;
   generating a graph of an average cardiac function of a normal heart;
   generating a standard cardiac motion contour image of the normal heart obtained from the graph of the average cardiac function of the normal heart with the ED contour image or the ES contour image being set as a base;
   superimposing the cardiac motion contour image on the standard cardiac motion contour image; and
   diagnosing an abnormal region in the subject heart from the superimposed state of the cardiac motion contour image of the subject heart and the standard cardiac motion contour image.

2. The method according to claim 1, wherein the step of forming a cardiac motion contour image comprises the steps of:
   continuously generating images of the subject heart;
   forming ED and ES contour images of the subject heart from said generated images; and
   superimposing the ED and ES contour images on each other.

3. The method according to claim 1 or 2, wherein the step of forming a cardiac motion contour image comprises the steps of:
   dividing the ED contour image into a predetermined number of first points, to form a predetermined number of first chords corresponding to the first points on the periphery of the ED contour image, said first chords extending perpendicularly from the ED contour image to the ES contour image;
   forming a first center line into connecting center points of the first chords;
   dividing the first center line into a predetermined number of second points and forming a predetermined number of second chords corresponding to the second points on the periphery of the first center line, said second chords extending perpendicularly from the ED contour image to the ES contour image; and
   measuring the length of each of the second chords and normalizing the measured length with the length of the periphery of the ED contour image.

4. The method according to claim 3, wherein the step of generating a graph of an average cardiac function comprises the steps of:
   calculating a plurality of cardiac function graphs relative to a plurality of persons having a normal heart;
   calculating an average cardiac function graph from the cardiac function graphs;
   calculating a standard deviation graph; and
   adding and subtracting the standard deviation graph to and from the average cardiac function graph, to form a cardiac function graph having upper and lower standard deviations.

5. The method according to claim 4, wherein the step of generating a standard cardiac motion contour image comprises the steps of:
   forming a standard ES contour image from the ED contour image of the subject heart;
   dividing the ED contour image into a plurality of points;
   forming a plurality of standard chords from the plurality of points of the ED contour image;
   extending the standard chords from the ED contour image by the length of the upper and lower standard deviations of the cardiac function graph; and
   connecting the points along the periphery of the ED contour image to form a standard contour image.

6. The method according to claim 1, 2, 4 or 5, wherein the step of superimposing comprises the step of superposing the standard cardiac motion contour image and said ED contour image of the subject heart one over another.

7. The method according to claim 1 or 2, wherein the standard cardiac motion contour image includes a predetermined number of chords, said chords being superimposed on the Ed contour image and extending inward to a central point of the ED contour image.

8. The method according to claim 1 or 2, wherein the chords extend inward toward a predetermined point in said ED contour image.

9. An apparatus for analyzing a ventricular function of a subject heart, comprising:
   means for forming an ED contour image representing a contour of the subject heart in an end diastole (DE) phase and an ES contour image in an end systole (ES) phase;
   means for forming a cardiac motion contour image using the ED contour image and the ES contour image;
   means for generating a graph of an average cardiac function of a normal heart;
   means for generating a standard cardiac motion contour image obtained by the graph of the average cardiac function of the normal heart with the ED contour image or the ES contour image being set as a base;
   means for superimposing the cardiac motion contour image on the standard cardiac motion contour image; and
   means for diagnosing an abnormal region of the subject heart from the superimposed cardiac motion contour image of the subject heart and the standard cardiac motion contour image.

10. The apparatus according to claim 9, wherein said means for forming a cardiac motion contour image comprises means for continuously generating images of the subject heart, means for forming ED and ES contour images of the heart from said images, and means for superimposing the ED and ES contour images on each other with longitudinal lines thereof being coincided.

11. The apparatus according to claim 9, wherein the means for forming a cardiac motion contour image comprises means for dividing the ED contour image into a predetermined number of first points to form a predetermined number of first chords corresponding to the first points on the periphery of the ED contour image, said first chords extending perpendicularly from the ED contour image to the ES contour image, means for forming a first center line by connecting center points of the first chords, means for dividing the first center line into a predetermined number of second points and forming a predetermined number of second chords corresponding to the second points on the periphery of the first center line, said second chords extending perpendicularly from the ED contour image to the ES contour image, and means for measuring the length of each of the second chords and normalizing the measured length with the length of the periphery of the ED contour image.

12. The apparatus according to claim 11, wherein said means for generating a graph of an average cardiac function comprises means for calculating a plurality of cardiac function graphs relative to a plurality of persons having a normal heart, means for calculating the average cardiac function graph from the cardiac function graphs, means for calculating a standard deviation graph, and means for adding and subtracting the standard deviation graph to and from the average cardiac function graph, to form a cardiac function graph having upper and lower standard deviations.

13. The apparatus according to claim 12, wherein said means for generating a standard cardiac motion contour image comprises means for forming a standard ES contour image from the ED contour image of the subject heart, to form standard chords therefrom, means for obtaining points extending the standard chords from the ED contour image by the length of the upper and lower standard deviations of the cardiac function graph, and means for connecting the points along the periphery of the ED contour image to form a standard contour image.

14. The apparatus according to claim 9, 11, 12 or 13, wherein said means for superimposing comprises means for superimposing the standard cardiac motion contour image on said ED contour image of the subject heart.

15. The apparatus according to claim 9 or 10, wherein the standard cardiac motion contour image includes a predetermined number of chords, said chords being superimposed on the ED contour image in a manner to extend inside from the ED contour image.

16. The apparatus according to claim 9 or 10, wherein the chords extend inward toward a predetermined point in said ED contour image.

* * * * *

UNITED STATES PATENT AND TRADEMARK OFFICE
CERTIFICATE OF CORRECTION

PATENT NO. : 5,065,435                           Page 1 of 2

DATED      : November 12, 1991

INVENTOR(S) : Mitsuo Oe

It is certified that error appears in the above-identified patent and that said Letters Patent is hereby corrected as shown below:

```
Abstract, line 2, after "steps" change "for" to --of--.
Abstract, line 9, change "S" to --ES--, and Delete
"to be".
Abstract, line 10, Delete "examined,".
Claim 1, column 5, line 27, change "(DE)" to --(ED)--.
Claim 1, column 5, line 28, after "forming" change
"and" to --an--.
Claim 3, column 5, line 63, change "into" to --by--.
Claim 7, columnn 6, line 43, change "Ed" to --ED--.
Claim 9, column 6, line 52, change "(DE)" to --(ED).
Claim 12, column 8, line 4, after "graph" change
"." to --,--.
```

UNITED STATES PATENT AND TRADEMARK OFFICE
CERTIFICATE OF CORRECTION

PATENT NO. : 5,065,435
DATED : November 12, 1991
INVENTOR(S) : Mitsuo Oe

It is certified that error appears in the above-indentified patent and that said Letters Patent is hereby corrected as shown below:

```
Claim 12, column 8, line 6, after "graph" Delete ",".
Claim 13, column 8, line 12, after "heart" Delete ",".
```

Signed and Sealed this

Twenty-fourth Day of August, 1993

Attest:

BRUCE LEHMAN

Attesting Officer

Commissioner of Patents and Trademarks